(12) United States Patent
Shibutani et al.

(10) Patent No.: US 8,721,966 B2
(45) Date of Patent: May 13, 2014

(54) CHEMICAL ANALYZER, METHOD FOR DISPENSING AND DILUTION CUP

(75) Inventors: Hitoshi Shibutani, Otawara (JP); Naoto Sato, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 73 days.

(21) Appl. No.: 12/716,332

(22) Filed: Mar. 3, 2010

(65) Prior Publication Data
US 2010/0158755 A1 Jun. 24, 2010

Related U.S. Application Data

(62) Division of application No. 12/106,906, filed on Apr. 21, 2008, now Pat. No. 7,897,409, which is a division of application No. 10/943,245, filed on Sep. 17, 2004, now abandoned.

(30) Foreign Application Priority Data

Sep. 19, 2003 (JP) ................ P2003-328603

(51) Int. Cl.
*G01N 1/38* (2006.01)
*G01N 35/00* (2006.01)
(52) U.S. Cl.
USPC .......................................... 422/68.1; 422/81
(58) Field of Classification Search
None
See application file for complete search history.

(56) References Cited

U.S. PATENT DOCUMENTS

| | | | |
|---|---|---|---|
| 5,443,791 A * | 8/1995 | Cathcart et al. | 422/65 |
| 2004/0067164 A1* | 4/2004 | VanBrunt et al. | 422/63 |
| 2005/0124059 A1* | 6/2005 | Kureshy et al. | 435/287.2 |
| 2005/0214172 A1* | 9/2005 | Burgisser | 422/100 |

FOREIGN PATENT DOCUMENTS

WO   WO 03099442 A1 * 12/2003

OTHER PUBLICATIONS

Slanina, J. et al. "Complexometric determination of 100 ng to 160 micrograms of calcium by means of a rapid automatic titrator." Z. Anal. Chem. (1972) 260 354-359.*

* cited by examiner

*Primary Examiner* — Christopher A Hixson
(74) *Attorney, Agent, or Firm* — Oblon, Spivak, McClelland, Maier & Neustadt, L.L.P.

(57) ABSTRACT

A method for dispensing a sample solution and a reagent into a container in a chemical analyzer includes a first step of dispensing a reagent into a container, a second step of dispensing a sample solution into the container after the first step, and a third step of dispensing the reagent into the container after the second step. A dilution cup includes an inner face where a diameter of a horizontal section increases on at least one position from a bottom to a top, an opening portion surrounding an opening, where a sample solution is dispensed, located on or near the top, a reagent aperture portion surrounding an aperture where a reagent is dispensed such that the sample solution and the reagent create an upswing spiral flow, and a drain aperture portion surrounding a drain aperture, where a mixed solution of the sample solution and the reagent is discharged, located on or near the bottom.

5 Claims, 5 Drawing Sheets

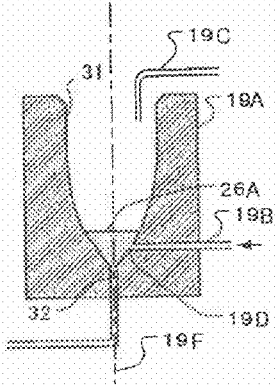 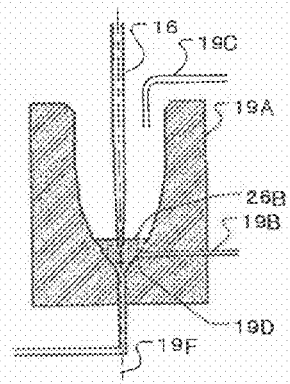 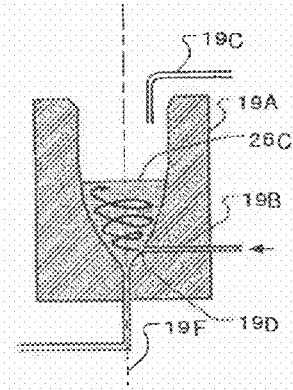
FIG. 3A  FIG. 3B  FIG. 3C
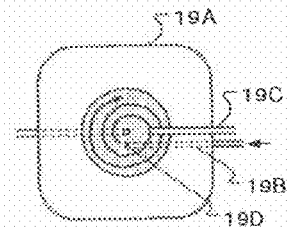
FIG. 3D

US 8,721,966 B2

CHEMICAL ANALYZER, METHOD FOR DISPENSING AND DILUTION CUP

CROSS-REFERENCE TO RELATED APPLICATIONS

This application is a divisional of and claims the benefit of priority under 35 USC §120 from U.S. application Ser. No. 12/106,906, filed Apr. 21, 2008 which is a divisional of U.S. application Ser. No. 10/943,245, filed Sep. 17, 2004 and is based upon and claims the benefit of priority from prior Japanese Patent Application No. 2003-328603 filed on Sep. 19, 2003, the entire contents of which are incorporated herein by reference.

FIELD OF THE INVENTION

The present invention relates generally to a chemical analyzer, a method for dispensing and a dilution cup.

BACKGROUND

Generally, a chemical analyser automatically analyses a chemical composition included in blood or urine of a human body, for example. A sample solution and a reagent are dispensed into a reaction cuvette. The chemical analyser measures, as one of biochemistry test arrays, concentration/activity of a substance to be measured or enzyme in the sample solution by measuring amount of penetration of light in order to obtain a change of color tone caused by reaction of a mixed solution of the sample solution and the reagent corresponding to the biochemistry test array.

Moreover, as other biochemistry test arrays, the chemical analyser measures concentration of sodium ion or potassium ion or chlorine ion in a sample solution dispensed into a dilution cup by measuring a change of electromotive force with an ion sensor about a mixed solution of the sample solution and a reagent. In this case, the reagent is used for dilution of the sample solution or adjustment of pH.

Major measurement error which is common to many biochemistry test arrays is caused when the sample solution and the reagent are dispensed and mixed to be uniformed.

There are two dispensing methods of the sample solution and the reagent. One method is a dispensing-first-sample solution method and another is a dispensing-first-reagent method. Both methods have the problems described below, respectively.

In the dispensing-first-sample solution method, the sample solution is dispensed into a container, and subsequently the reagent is dispensed into the container to be mixed with the sample solution.

The dispensing-first-sample solution method is classified into two methods, a non-contacting dispensing method and a contacting dispensing method.

When amount of the sample solution used for each biochemistry test array was large, the non-contacting dispensing method where the sample solution was dispensed into the container from a sample dispensing probe that was away from the container is applied.

However, at the present the amount of the sample solution used for each biochemistry test array is little. Therefore, as the contact dispensing method, the sample solution is dispensed into the container from a sample dispensing probe that is contacting the container has been applied, since the sample solution that should be dispensed into the container is adhered to the outside of the sample dispensing probe or flies in all directions and the sample solution is not dispensed into an appropriate part of the container in the non-contacting dispensing method. The contacting dispensing method is described in Japanese Patent 61-56784 (KOUKOKU) (page 4-5 and FIG. 4-5).

However, in the contacting dispensing method, the sample solution dispensed into the container does not spread into the container depending on the circumstances where stain remains or a bottom form where the sample dispensing probe contacts the container influences the spread. As described above, the sample solution is not dispensed well.

In order to reduce the problem of the bottom form of the container, high processing accuracy to make the container is required. Especially, in the chemical analyser including a plurality of containers, such as reaction cuvettes, it is difficult to achieve the high processing accuracy. In order to reduce another problem of the remain of the stain, a high flushing capacity is required.

On the other hand, in the dispensing-first-reagent method, the reagent is first dispensed into the container, and the sample solution is dispensed into the container to be mixed with the reagent. The dispensing-first reagent method is described in Japanese Patent Disclose (KOKAI) (page 3).

In the dispensing-first-reagent method, when the sample dispensing probe directly contacts the reagent, or the sample dispensing probe does not contact the reagent but a drop located on a top of the sample dispensing probe contacts a surface of the reagent, the sample solution is poured from the sample dispensing probe into the reagent. The sample solution is not adhered to the outside of the sample dispensing probe or does not fly off, and therefore, the dispensing-first-reagent method is adapted at the present when the amount of the sample solution is little.

The dispensing-first-reagent method needs a more powerful mixing unit than that in the dispensing-first-sample solution method, in order to mix the sample solution and the reagent to be uniformed. However, a speedy measurement or a speedy mixing is required recently, and it is difficult to achieve the required speed even with the powerful mixing unit.

In the chemical analyzer, it is required that the amount of the sample solution used for each biochemistry test array is reduced, and the sample solution is dispensed well.

However, as described above, in the dispensing-first-sample solution method, the bottom form of the container or the remaining stain can be major error factor, and in the dispensing-first-reagent, the powerful mixing unit is required.

SUMMARY

One object of the present invention is to ameliorate the above-mentioned problems. According to one aspect of the present invention, there is provided a method for dispensing a sample solution and a reagent into a container in a chemical analyser includes a first step of dispensing a reagent into a container, a second step of dispensing a sample solution into the container after the first step, and a third step of dispensing the reagent into the container after the second step.

According to another aspect of the present invention, there is provided a dilution cup includes an inner face where a diameter of a horizontal section increases on at least one position from a bottom to a top, an opening portion surrounding an opening, where a sample solution is dispensed, located on or near the top, a reagent aperture portion surrounding an aperture where a reagent is dispensed such that the sample solution and the reagent create an upswing spiral flow, and a drain aperture portion surrounding a drain aperture, where a mixed solution of the sample solution and the reagent is discharged, located on or near the bottom.

According to another aspect of the present invention, there is provided a chemical analyser includes a container where a sample solution and a reagent are mixed, a first mechanism configured to dispense the reagent into the container, a second mechanism configured to dispense the sample solution in to the container, and a controller configured to control the first mechanism to dispense the reagent in a first step, the second mechanism to dispense the sample solution in a second step after the first step, and the first mechanism to dispense the reagent in a third step after the second step.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings:

FIGS. 3A through 3D are illustrations for explaining an operation of dispensing solution into a dilution cup according to the embodiment;

DETAILED DESCRIPTION OF EXEMPLARY EMBODIMENTS

Referring to FIGS. 1 through 5, an embodiment of a chemical analyzer, a method for dispensing and a dilution cup are explained.

Figure 1:
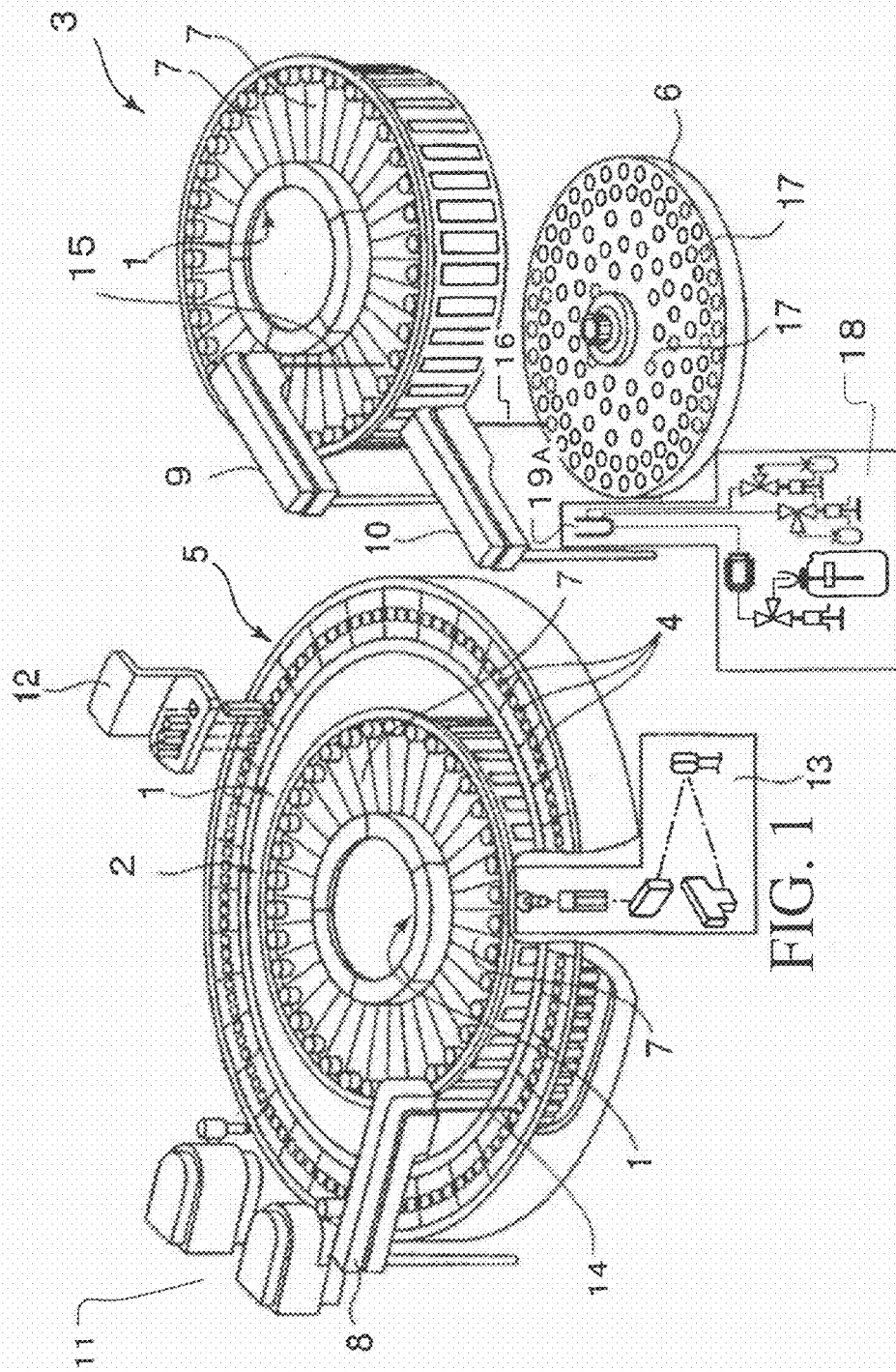
FIG. 1 is a perspective view of a chemical analyzer according to an embodiment.

FIG. 1 shows a perspective view of a chemical analyser of the embodiment.

The chemical analyser includes a reagent rack 1 for supporting a plurality of reagent bottles 7 where a reagent to be reacted with substance of a sample solution is included, reagent storages 2 and 3 which can hold the reagent rack 1, a reaction click 5 for supporting a plurality of reaction cuvettes. The reaction cuvettes are supported on a circumference of the reaction disk 5. Further, the chemical analyser includes a disk sampler 6, a first reagent dispensing arm 8, a second reagent dispensing arm 9, a sample dispensing arm 10, a photometric measurement unit 13 and an electrolyte measurement module 18. The disk sampler 6 supports a plurality of sample solution bottles 17, each of which includes the sample solution are set. The photometric measurement unit 13 measures a mixed solution of the reagent and the sample solution which are dispensed into reaction cuvette 4 via the reagent dispensing arm 8 or 9 and the sample dispensing arm 10, respectively. The electrolyte measurement module 18 measures a sample solution dispensed into a dilution cup 19A via the sample dispensing arm 10.

The reagent storages 2 and 3, the reaction disk 5 and the disk sampler 6 are rotatable by a driving unit.

The reagent for the measurement is pulled out from the reagent bottle 7 and is dispensed into the reaction cuvette 4 by a first reagent probe 14 of the first reagent dispensing arm 8 or a second reagent probe 15 of the second reagent dispensing arm 9.

The sample solution for the measurement is pulled out from the sample solution bottle 17 and is dispensed into the reaction cuvette 4 or the dilution cup 19A by a sample dispensing probe 16 of the sample dispensing arm 10.

The reaction cuvette 4 where the sample solution and the reagent are dispensed rotates and moves to such a position that a mixing unit 11 mixes the sample solution and the reagent.

The photometric measurement unit 13 irradiates a light to the reaction cuvette 4 which moves to a photometric measurement position and measures a change of a light absorption of the mixed solution. In this measurement, at least one biochemistry test array other than sodium ion, potassium ion and chlorine ion in the sample solution is analysed.

After the analysis of the biochemistry test array, the mixed solution of the sample solution and the reagent in the reaction cuvette 4 is evacuated, and the reaction cuvette 4 is washed by a washing machine 12.

On the other hand, concentration of the electrolyte of the sodium ion or the potassium ion or the chlorine ion in a sample solution dispensed into the dilution cup 19A is measured by the electrolyte measurement module 18.

Figure 2:
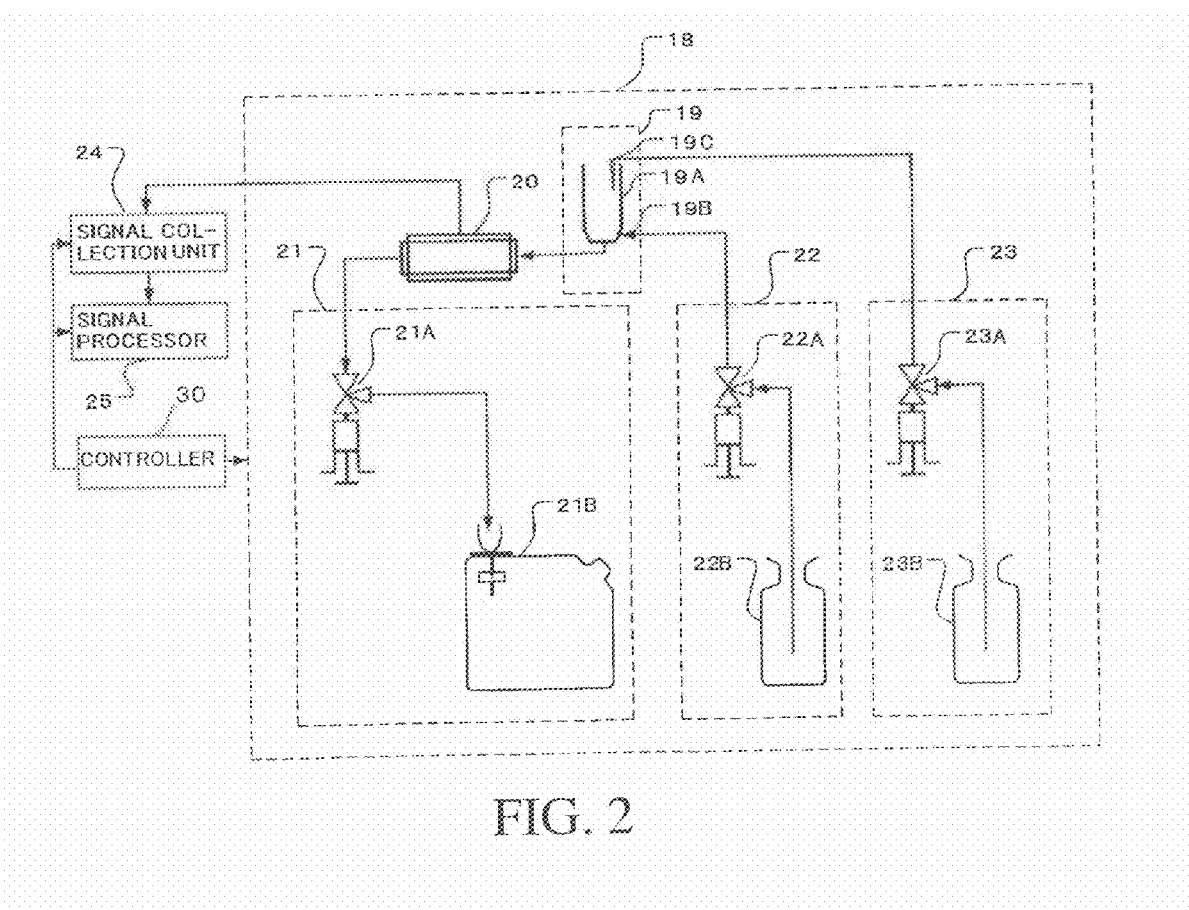
FIG. 2 is a block diagram of an electrolyte measurement module according to the embodiment.

FIG. 2 shows the electrolyte measurement module 18 shown in FIG. 1. The electrolyte measurement module 18 includes a dilution cup unit 19, a reagent supply unit 22, a calibration solution supply unit 23, a reagent suction unit 21, and a ion sensor unit 20. The dilution cup unit 19 is used for mixing the sample solution and the reagent. The reagent supply unit 22 and the calibration solution supply unit 23 supply the reagent and the calibration solution to the dilution cup unit 19, respectively. The reagent suction unit 21 supplies the mixed solution of the sample solution and the reagent or the calibration solution to the ion sensor unit 20 which measures the concentration of the electrolyte of the sodium ion or the potassium ion or the chlorine ion in the mixed solution of the sample solution and the reagent or the calibration solution.

The dilution cup unit 19 includes the dilution cup 19A as the container for mixing the sample solution and the reagent, a reagent charge port 19B used for dispensing the reagent into the dilution cup 19A, and a calibration solution charge nozzle 19C used for dispensing the calibration solution into the dilution cup 19A.

The reagent supply unit 22 pulls out the reagent from a reagent bottle 22B by using a reagent supply pump 22A, and supplies the reagent into the dilution cup 19 to dilute the sample solution.

The calibration solution supply unit 23 pulls out the calibration solution from a calibration solution bottle 23B by using a calibration solution supply pump 23A, and supplies the calibration solution into the dilution cup 19. The calibration solution is used for washing the dilution cup 19A to remove a remaining sample solution after the sample solution diluted in the dilution cup 19A flows into the ion sensor unit 20, and is used for calibrate an electromotive force of the ion sensor unit 20.

In the reagent suction unit 21, a reagent suction pump 21A leads the mixed solution diluted in the dilution cup 19A or the calibration solution to the ion sensor unit 20 and subsequently the mixed solution or the calibration solution are evacuated into a waste solution tank 21B.

In the ion sensor unit 20, the concentration of the electrolyte of the sodium ion, the potassium ion and the chlorine ion by a flow-through type composition electrode including a sodium ion sensor, a potassium ion sensor, a chlorine ion sensor and a reference electrode.

The following is a process for measuring the electrolyte. The sample solution dispensed into the dilution cup 19A by the sample dispensing probe 16 shown in FIG. 1 is mixed to the reagent supplied from the reagent supply unit 22. Thereafter, the mixed solution is fed to the ion sensor unit 20 by the reagent suction unit 21 so that the electrolyte is measured.

The ion sensor unit 20 generates an electronic signal according to the concentration of a target ion. The electronic signal is collected by a signal collection unit 24, and is used for calculation process of the sample solution in a signal processor 25.

Next, the calibration solution is fed to the ion sensor unit 20 by the calibration solution supply unit 23, and the electrolyte in the calibration solution is measured. When a result of the measurement of the calibration solution is compared with a result of the measurement of the sample solution, the concentration of the electrolyte is obtained.

After the measurement, each solution fed to the ion sensor unit 20 is evacuated by the reagent suction unit 21.

An operation sequence of the reagent suction pump 21A, the reagent supply pump 22A, and the calibration solution supply pump 23A, and a process of the signal generated in the ion sensor unit 20 are controlled by a controller according to a program stored in a memory unit of the chemical analyser in advance.

FIG. 3A through 3D show illustrations for explaining a process for dispensing the same reagent twice into the dilution cup 19A.

FIG. 3A through 3C are sectional views of the dilution cup 19A. At the bottom of the dilution cup, a drain aperture 32 to the ion sensor unit 20 is located. In an inner face of the dilution cup 19A, a cross section which is substantially perpendicular to a vertical central axis 19F which is located at a center of the dilution cup 19A is circular form. A diameter of the circular form gradually increases from the bottom to a top of the dilution cup 19A. A cross section which is substantially parallel to the vertical central axis in the inner face is a gradual curved surface, like a hanging bell.

The reagent charge port 19B is located at a position slightly above the bottom of the dilution cup 19A, and extends horizontally. An reagent charge aperture 19D connects the reagent charge port 19B to the inner face of the dilution cup 19A is located on a point on a circumference of the cross section which is substantially perpendicular to the vertical central axis 19F.

FIG. 3A shows an illustration for explaining a first step for dispensing first predetermined amount of the reagent into the dilution cup 19A.

For example, when a required amount of the reagent is 575 µl, the first predetermined amount 125 µl which is approximately 22% of the required amount is dispensed from the reagent charge port 19B into the dilution cup 19A. The reagent 26A is dispensed in the first step.

Speed for dispensing the reagent in the first step is controlled such that the reagent does not fly off from the dilution cup 19A by the reagent supply pump 22A.

FIG. 3B shows an illustration for explaining a second step for dispensing predetermined amount of the sample solution into the dilution cup 19A after the first step.

The sample dispensing arm 10 shown in FIG. 1 rotates such that the sample dispensing probe 16 is located above the dilution cup 19A and is located on the vertical central axis 19F. The sample dispensing probe 16 stops once at the position, and descends through an opening 31 which is located on the top of the dilution cup 19A. The sample dispensing probe 16 detects a surface of the reagent and stops at a depth of about 1 mm under the surface of the reagent to dispense 25 µl of the sample solution, for example. In the dilution cup 19A, an intermediate mixed solution of 25 µl of the sample solution and 125 µl of the reagent exists.

As described above, since the sample dispensing probe 16 soaks in the reagent 26A dispensed in the first step when the sample solution is dispensed, as the dispensing-first-reagent method, the sample solution is not adhered to the outside of the sample dispensing probe 16 or does not fly off, and therefore, the dispensing is performed well.

FIG. 3C shows an illustration for explaining a third step for dispensing second predetermined amount of the reagent into the dilution cup 19A.

After dispensing the sample solution into the dilution cup 19A, the remaining amount 450 µl of the reagent is dispensed from the reagent charge port 19B by the reagent supply pump 22A to be uniformly mixed with the intermediate mixed solution 26B. Finally, the mixed solution 26C of the sample solution and the reagent exists.

In the third step, the reagent, 78% of the required reagent, namely 450 µl, which is more than that of the first step is dispensed. In addition, the reagent is dispensed from the reagent charge aperture 19D into the upside down hanging bell formed dilution cup 19A under the control to create an upswing spiral flow indicated as an allow in FIG. 3C and FIG. 3D which shows an upper view of the dilution cup 19A. Thereby, an effective mixing can be performed.

Subsequently, the mixed solution 26C is fed to the ion sensor unit 20 via the drain aperture 32 by the reagent suction unit 21 so that the electrolyte is measured in the sample solution.

An operation of the sample dispensing arm 10 and the sample dispensing probe 16 is controlled by the controller according to a program stored in a memory unit of the chemical analyser in advance so as to work with the operation of each pump described above.

Figure 4A:
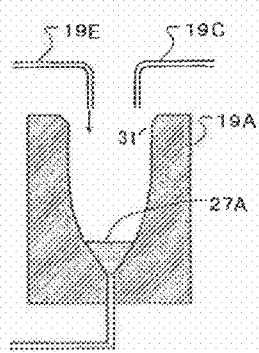
FIGS. 4A through 4C are illustrations for explaining an operation of dispensing solution into a dilution cup according to a modification of the embodiment.
Figure 4B:
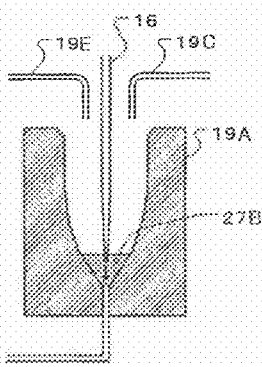
Figure 4C:
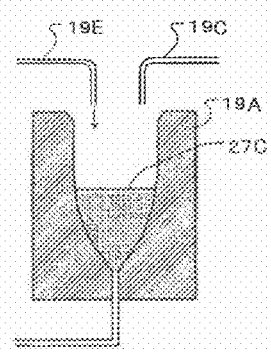

FIG. 4A through 4C show illustrations for explaining a process for dispensing the same reagent twice into a commonly used dilution cup 19A, as a modification. The difference between FIG. 3A through 3C and FIG. 4A through 4C is a position of a reagent charge port. In FIG. 3A through 3C, the reagent charge port 19B is located near the bottom of the dilution cup 19A, however in FIG. 4A through 4C, the reagent charge port 19e is locate above the dilution cup 19A.

FIG. 4A shows an illustration for explaining a first step for dispensing first predetermined amount of the reagent. When a required amount of the reagent is 575 µl, the first predetermined amount 125 µl which is approximately 22% of the required amount is dispensed from the reagent charge port 19E into the dilution cup 19A. The reagent 27A is dispensed in the first step.

Speed for dispensing the reagent in the first step is controlled such that the reagent does not fly off from the dilution cup 19A by the reagent supply pump 22A.

FIG. 4B shows an illustration for explaining a second step for dispensing predetermined amount of the sample solution into the dilution cup 19A after the first step.

The sample dispensing arm 10 shown in FIG. 1 rotates such that the sample dispensing probe 16 is located above the dilution cup 19A and is located on the vertical central axis 19F. The sample dispensing probe 16 stops once at the position, and descends through an opening 31 which is located on the top of the dilution cup 19A. The sample dispensing probe 16 detects a surface of the reagent and stops at a depth of about 1 mm under the surface of the reagent to dispense 25 µl of the sample solution, for example. In the dilution cup 19A, an intermediate mixed solution of 25 μl of the sample solution and 125 μl of the reagent exists.

As described above, since the sample dispensing probe 16 soaks in the reagent 27A dispensed in the first step when the sample solution is dispensed, as the dispensing-first-reagent method, the sample solution is not adhered to the outside of the sample dispensing probe 16 or does not fly off, and therefore, the dispensing is performed well.

FIG. 4C shows an illustration for explaining a third step for dispensing second predetermined amount of the reagent into the dilution cup 19A.

After dispensing the sample solution into the dilution cup 19A, the remaining amount 450 μl of the reagent is dispensed from the reagent charge port 19E by the reagent supply pump unit 22 to be uniformly mixed with the intermediate mixed solution 26B. Finally, the mixed solution 27C of the sample solution and the reagent exists.

In the third step, the reagent, 78% of the required reagent, namely 450 μl, which is more than that of the first step is dispensed. In addition, the dispensing of the reagent is controlled such that the speed of the dispensing is as much as possible within a range where the reagent does not fly off. Thereby, the reagent and the sample solution are mixed to be uniformed, and finally the mixed solution 27C exists.

Subsequently, the mixed solution 27C is fed to the ion sensor unit 20 by the reagent suction unit 21 so that the electrolyte is measured in the sample solution.

The above mentioned method is effective especially to the electrolyte measurement where high precision of dispensing of the reagent and the sample solution is required.

Figure 5A:
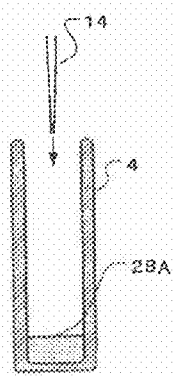
FIGS. 5A through 5C are illustrations for explaining an operation of dispensing solution into a reaction cuvette according to the embodiment.
Figure 5B:
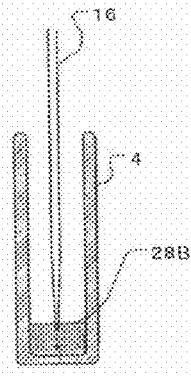
Figure 5C:
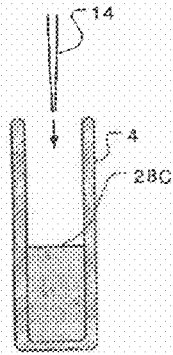

FIG. 5A through 5C show illustrations for explaining a process for dispensing the same reagent twice into the reaction cuvette 4.

FIG. 5A shows an illustration for explaining a first step for dispensing first predetermined amount of the reagent into the reaction cuvette 4.

The first reagent probe 14 shown in FIG. 1 pulls out a first reagent corresponding to a biochemistry test array, and the first reagent dispensing arm 8 rotates such that the first reagent moves to a position for dispensing. When the lower limit of the amount of the first reagent which is required for photometric measurement of the photometric measurement unit 13 is 120 μl, one third of 120 μl, namely 40 μl of the first reagent is dispensed into an approximate center of the reaction cuvette 4. In this first step, the reagent 28A exists in the reaction cuvette 4. Thereafter, the reaction disk 5 rotates such that the reaction cuvette 4 moves to such a position that the sample solution is dispensed.

Speed of dispensing of the reagent in the first step is controlled not to fly off to a side inner face of the reaction cuvette 4.

FIG. 5B shows an illustration for explaining a second step for dispensing predetermined amount of the sample solution into the reaction cuvette 4 after the first step.

The sample dispensing arm 10 shown in FIG. 1 rotates such that the sample dispensing probe 16 is located above a centor of the reaction cuvette 4. The sample dispensing probe 16 stops once at the position, descends to the reaction cuvette 4, and detects a surface of the reagent 28A. The sample dispensing probe 16 stops at a depth of about 1 mm under the surface of the reagent 28A to dispense the predetermined amount of the sample solution. In the reaction cuvette 4, an intermediate mixed solution 28B of the predetermined amount of the sample solution and the 40 μl of the reagent exists. Thereafter, the reaction disk 5 rotates such that the reaction cuvette 4 is located at a position for dispensing the same reagent as that in the first step once again. The above operation is controlled by a controller 30.

As described above, since the sample dispensing probe 16 soaks in the reagent 28A dispensed in the first step when the sample solution is dispensed, as the dispensing-first-reagent method, the sample solution is not adhered to the outside of the sample dispensing probe 16 or does not fly off, and therefore, the dispensing is performed well.

FIG. 5C shows an illustration for explaining a third step for dispensing second predetermined amount of the reagent into the reaction cuvette 4.

The first reagent probe 14 that pulls up the reagent fro the reagent storages 2 and rotates to be located at a second reagent dispensing position for dispensing the reagent once again. When the reaction cuvette 4 stops at the second reagent dispensing position, the second predetermined amount of the reagent, such as more than two thirds of the required amount, is dispensed into an approximate centor of the reaction cuvette 4. Thereby, the second dispensed reagent is mixed with the intermediate mixed solution to be a mixed solution 28C.

The reaction disk 5 rotates so that the reaction cuvette 4 moves to a position to be mixed by the mixing unit 11. The mixing unit 11 further mixes the mixed solution 28C.

In the third step, the second amount of the reagent which is more than that in the first step is dispensed, and speed of the dispensing is as much as possible within a range where the reagent does not fly off. Thereby, the reagent and the sample solution are mixed to be uniformed.

When two kinds of the reagent are required for measurement, the reaction disk 5 rotates and stops, and the second reagent probe 15 pulls a second reagent corresponding to a biochemistry test array from the reagent storage 3. Thereafter, the second reagent dispensing arm 9 rotates, and the second reagent is dispensed into the reaction cuvette 4 by the second reagent probe 15.

The photometric measurement unit 13 irradiates the light to the reaction unit for a predetermined time, and detects the change of the light passing through the sample solution.

The above mentioned method is effective especially to the electrolyte measurement where high precision of dispensing of the reagent and the sample solution is required.

The chemical analyser may have a memory which stores information of relationship between the required total amount of the reagent and the amount of the reagent dispensed in the first step. In the memory, the speed of dispensing of the reagent in the first and third steps may be stored instead of or in addition to the amount relationship information. The above mentioned separate dispensing method may be selected by each biochemistry test array. The speed of dispensing of the reagent in the third step may be faster than that of the first step, and thereby, more effective mixing can be performed.

The present invention may be not limited to the above embodiments, and various modifications may be made without departing from the spirit or scope of the general inventive concept.

What is claimed is:

1. A chemical analyser, comprising:
   a container where a sample solution and a reagent are mixed;
   a sample solution dispensing unit configured to execute a dispensing operation, which includes an aspiration of a sample and a discharge of the aspirated sample into the container by a sample dispensing probe;
   a detecting unit configured to detect a surface of the reagent;

a reagent dispensing unit configured to execute a dispensing operation, which includes an aspiration of the reagent and a discharge of the aspirated reagent into the container by a reagent dispensing probe; and a controller configured to control the reagent dispensing unit to dispense the reagent by the reagent dispensing probe in a first step, and to control the sample dispensing unit to descend and stop in the position where the end of the dispensing probe is at a predetermined depth under the surface of the reagent in the container and to dispense the sample solution in a second step after the first step, and to control the reagent dispensing unit to dispense the reagent by the reagent dispensing probe in a third step after the second step;

wherein the controller controls the reagent dispensing unit such that amount of the reagent dispensed in the first step is smaller than amount of the reagent dispensed in the third step and the concentration of the reagent dispensed in the third step is the same as the concentration of reagent in the first step.

2. The chemical analyser according to claim 1, wherein the controller controls speed of dispensing of the reagent and the sample solution.

3. The chemical analyser according to claim 2, wherein the speed of dispensing of the reagent in the third step is faster than the speed of dispensing of the reagent in the first step.

4. The chemical analyser according to claim 1, wherein the container is a dilution cup.

5. The chemical analyser according to claim 1, wherein the container is a reaction cuvette.

* * * * *